(12) United States Patent
Hooker et al.

(10) Patent No.: US 6,519,356 B1
(45) Date of Patent: Feb. 11, 2003

(54) SYSTEM AND METHOD FOR INSPECTING CANS

(75) Inventors: Jeff Hooker, Melbourne, FL (US); James Spencer, Oviedo, FL (US); Jeff Starnes, Merritt Island, FL (US); Ed Tajudeen, Oviedo, FL (US); Jim Kirk, Port St. John, FL (US); Tim Hebert, Orlando, FL (US); Steve Simmons, Melbourne, FL (US)

(73) Assignee: Intelligent Machine Concepts, L.L.C., Titusville, FL (US)

( * ) Notice: Subject to any disclaimer, the term of this patent is extended or adjusted under 35 U.S.C. 154(b) by 0 days.

(21) Appl. No.: 09/366,407

(22) Filed: Aug. 3, 1999

(51) Int. Cl.[7] .................................................. G06K 9/00
(52) U.S. Cl. .................... 382/143; 382/143; 356/239.4; 209/526; 209/524; 348/127
(58) Field of Search ................................. 382/143, 149, 382/172, 286, 289, 312; 356/239.4, 239.5, 239.6, 427, 428, 240, 23; 209/526, 523, 707, 539, 524, 701, 538, 656, 651–654, 939, 936; 198/370, 372, 406, 409, 410; 348/127

(56) References Cited

U.S. PATENT DOCUMENTS

| | | | | |
|---|---|---|---|---|
| 4,108,762 A | * | 8/1978 | Babunovic et al. | 209/524 |
| 4,385,699 A | * | 5/1983 | Ashina | 209/538 |
| 4,601,395 A | * | 7/1986 | Juvinall et al. | 250/223 B |
| 4,697,245 A | | 9/1987 | Kara et al. | 364/552 |
| 4,906,099 A | | 3/1990 | Casasent | 356/394 |
| 4,915,237 A | | 4/1990 | Chang et al. | 209/524 |
| 4,924,107 A | * | 5/1990 | Tucker | 250/559.46 |
| 5,095,204 A | * | 3/1992 | Novini | 250/223 B |
| 5,141,111 A | * | 8/1992 | Licht | 209/558 |
| 5,280,436 A | | 1/1994 | Kubota et al. | 364/559 |
| 5,371,690 A | | 12/1994 | Engel et al. | 364/570 |
| 5,699,152 A | | 12/1997 | Fedor et al. | 356/237 |
| 5,742,037 A | | 4/1998 | Scola et al. | 235/454 |
| 5,764,874 A | | 6/1998 | White | 396/155 |
| 5,807,449 A | | 9/1998 | Hooker et al. | 156/64 |
| 5,818,443 A | | 10/1998 | Schott | 382/141 |
| 5,880,772 A | | 3/1999 | Kalnajs et al. | 348/87 |
| 5,901,241 A | | 5/1999 | Koljonen et al. | 382/150 |
| 6,226,081 B1 | * | 5/2001 | Fantone et al. | 356/239.6 |

FOREIGN PATENT DOCUMENTS

| | | | |
|---|---|---|---|
| DE | 297 07 734 U1 | 5/1998 | G01N/21/90 |
| EP | 0 336 476 A1 | 3/1989 | G01N/21/90 |
| WO | WO 96/41299 | 12/1996 | G06K/9/00 |

* cited by examiner

*Primary Examiner*—Bhavesh Mehta
*Assistant Examiner*—Sheela Chawan
(74) *Attorney, Agent, or Firm*—Allen, Dyer, Doppelt, Milbrath & Gilchrist, P.A.

(57) ABSTRACT

A system and method inspects containers and cans and includes a conveyor for advancing a plurality of containers into an inspection area. A sensor senses when a can has advanced into the inspection area. At least one light source illuminates the exterior of the can and interior of the can through the top opening after sensing that a can has advanced into the inspection area. The top camera has a field of view looking down into the top opening for obtaining a pixel image of the top and interior of the can and opposing side cameras obtain pixel images in elevation of the container. A processor processes the pixel images and calculates eccentricity, diameter of the opening, and flange width measurements based on the pixel image of the top and the interior of the container. The processor calculates height and flange angle measurements based on the pixel images obtained in the elevation of the container. The processor includes a circuit for comparing the calculated measurements with a threshold measurement requirement.

33 Claims, 8 Drawing Sheets

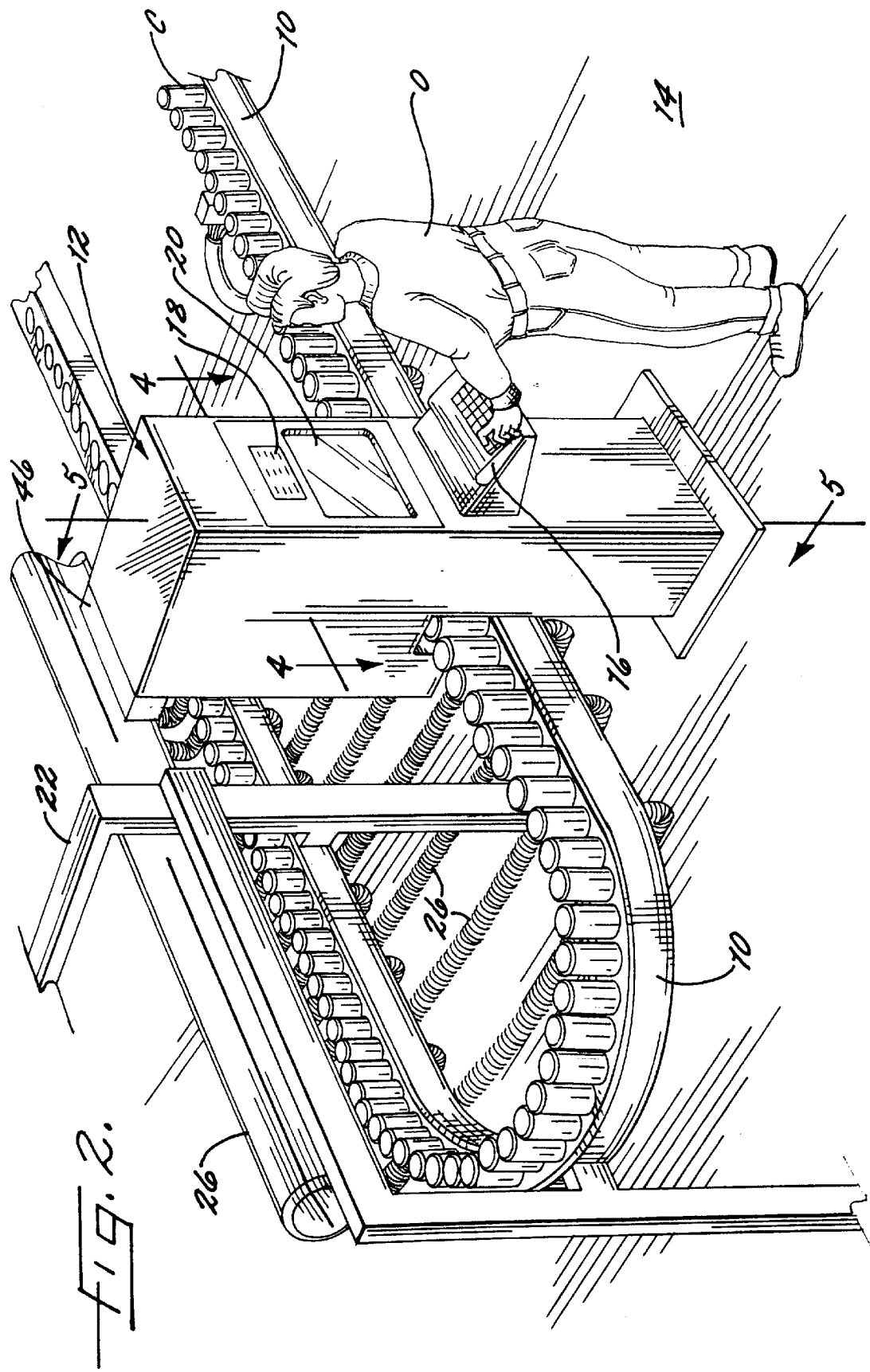

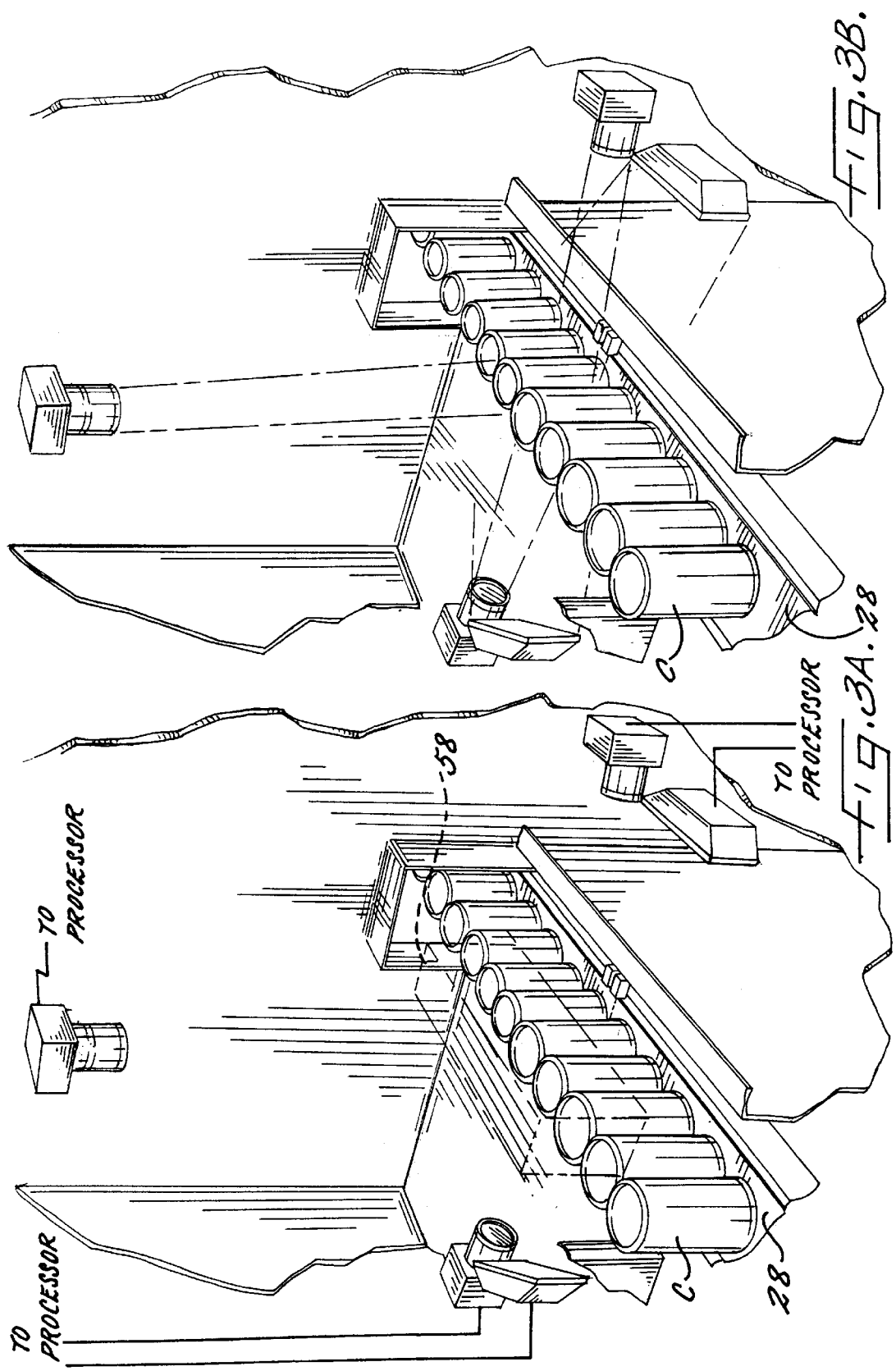

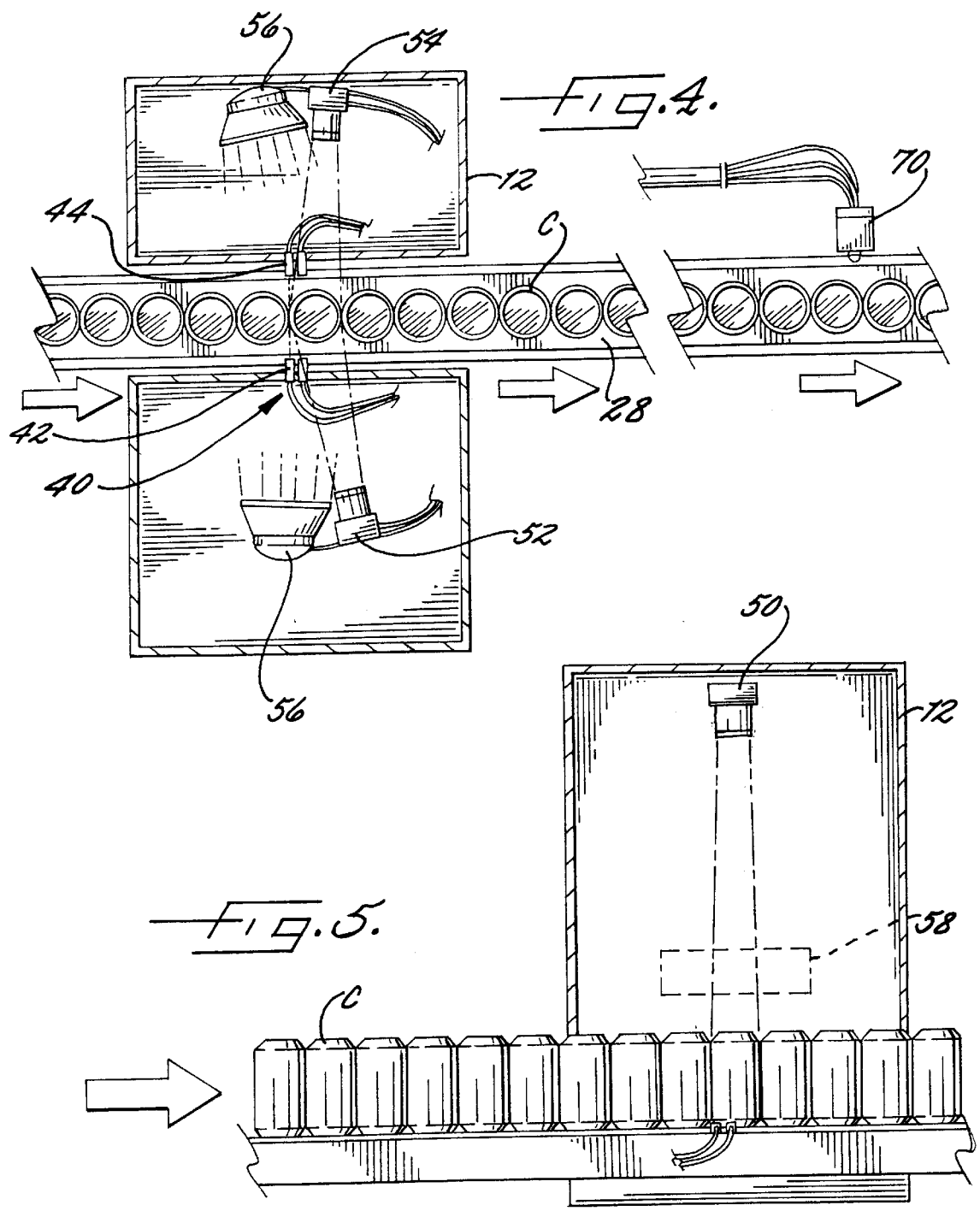

SYSTEM AND METHOD FOR INSPECTING CANS

FIELD OF THE INVENTION

This invention relates to the field of container inspection, and more particularly, this invention relates to the field of inspecting substantially cylindrical cans with open tops.

BACKGROUND OF THE INVENTION

Complicated container and can designs may include a substantially cylindrical top having an opening and inside surface. A flange is often formed at the top opening. An example is a standard beverage can, such as used for carbonated drinks and beer. In many can production lines, statistical process control is used for inspecting the containers and/or cans. Every eight hour shift, a number of different cans are selected and the dimensional height measurements and inside and outside diameter at the top opening, as well as the flange width and flange angle, are measured and compared with a standard. If the cans are off tolerance, then the die operation that produces the can upstream and the inspection equipment itself are analyzed and corrected, if necessary.

Recently, the demands brought about by worldwide competition and lower manufacturing and end-user costs require greater control over the can inspection process. Customers now demand 100% inspection of all cans, instead of the statistical process control inspection where in every shift, only a small number of cans are pulled from the processing line and inspected. This demand for inspecting every can is difficult in most high speed can and container manufacturing operations. Often up to 4.5 million cans are manufactured in a 24-hour shift, corresponding to about 50 cans a second. Thus, the cans are moving extremely fast in the processing station and inspection of each can must occur quickly and efficiently.

There are some prior art inspection systems that have been used for different products, such as cigarettes, as disclosed in U.S. Pat. No. 4,906,099 to Casasent, the disclosure which is hereby incorporated by reference in its entirety. Other inspection systems have been used on cans, but do not provide the desired high speed inspection for the top, interior, flange width and angles and elevation, especially in very high speed conveyor systems. Examples include U.S. Pat. No. 5,699,152 to Fedor et al., U.S. Pat. No. 4,924,107 to Tucker, and U.S. Pat. No. 4,697,245 to Kara et al., the disclosures which are hereby incorporated by reference in their entirety. Some of these systems are not amenable to high speed inspection of both top and sides of cans.

SUMMARY OF THE INVENTION

It is therefore an object of the present invention to provide a system and method for inspecting containers and cans, such as the type of beverage can having an inside surface and substantially cylindrical top opening and flange formed at the top opening, which allows inspection of every can at high operating speeds.

It is still another object of the present invention to provide a system and method for inspecting containers and cans that minimizes system complexity while allowing high speed inspection.

In accordance with the present invention, a system allows inspection of containers and cans at high operating speeds such as 50 cans a second. A conveyor advances a plurality of containers along a predetermined path of travel into an inspection area, where an inspection station is positioned. Each container includes an inside surface and a substantially cylindrical top opening and a flange formed at the top opening. In the case of cans, the container is cylindrically configured. A sensor senses when a container has advanced into the inspection area. At least one light source illuminates the exterior of the container and the interior of the container through the top opening after sensing that a container has advanced into the inspection area. A camera is located at the inspection area and has a field of view looking down into the top opening for obtaining a pixel image of the top and interior of the container.

Opposing side cameras are positioned on respective sides of the conveyor at the inspection area and have a field of view in elevation of the container for obtaining pixel images in elevation of the container. Appropriate processing software, such as operating with a digital signal processor that is connected to the sensor and top and side cameras, process the pixel images and calculate the eccentricity, diameter of the opening and flange width measurements based on the pixel image of the top and interior of the container. The processor also calculates height and flange angle measurements based on the pixel images obtained in elevation of the container. The processor includes a circuit for comparing the calculated measurements to a threshold measurement requirement. Cans can be rejected downstream at an ejection station, such as a pneumatic blow off, if the calculated measurements are not within a threshold measurement requirement.

In accordance with another aspect of the present invention, the system includes a circuit for processing the pixel image obtained from the top camera and calculates the inside and outside diameter of the opening. The system can include a backlight positioned adjacent each side camera and the light source can further comprise a strobe light. The cameras in one embodiment can comprise charge-coupled device (CCD) cameras. The sensor can include a beam sensor having a light source positioned on one side of the conveyor and a light receptor positioned on the other side of the conveyor. The conveyor can be formed to have vacuum holes that draw the can down to secure the can in vertical orientation on the conveyor. It is also possible to blow air upward from the conveyor and have containers moved by pressure from one container against the other. If the containers and cans are positioned in close proximity and even adjacent to each other, a can can be sensed by having a light beam from a light source extend to the light receptor, such as when the open crack area formed between two cans allows a light beam to extend from the light source to the light receptor.

In still another aspect of the present invention, the light source generates light on-axis with a vertically oriented can and into the interior of a can through the top opening after sensing that a can has advanced into the inspection area. The light source could include a beam splitter for providing light that is on-axis with the can. Spot lenses, such as coming from a plurality of fiber optic cables, could be used.

In still another aspect of the present invention, a method of inspection is provided to permit the inspecting of containers at high operating speeds. The method comprises the step of feeding a plurality of containers along a predetermined path of travel into an inspection station. The containers each include an inside surface having a substantially cylindrical top opening and a flange formed at the top opening. The method also comprises the step of sensing a container as it advances into the inspection station and illuminating the exterior of the container and its interior through the opening in response to the sensing of the container. Pixel images of the container can be obtained from the top camera having a field of view looking down into the top opening from two opposing side cameras and having a field of view in elevation onto the container.

The method can also comprise the step of processing the pixel images obtained from the top camera for calculating the eccentricity, the diameter of the opening, and the flange width measurements, and processing the pixel images obtained from the side cameras for calculating the height and flange angle measurements. The calculated measurements can be compared with the threshold measurement requirement and a container can be rejected when the container does not meet the threshold requirement.

BRIEF DESCRIPTION OF THE DRAWINGS

Other objects, features and advantages of the present invention will become apparent from the detailed description of the invention which follows, when considered in light of the accompanying drawings in which:

FIG. 2 is a more general isometric view of the system of the present invention showing the overall conveyor and inspection station, where an operator monitors the inspection process.

FIG. 3A is a schematic, isometric view of the interior of the inspection station showing top and opposing side cameras and back lights, and the on-axis lighting used at the top of the can.

FIG. 3B is another schematic, isometric view similar to FIG. 3A, and showing the camera operation.

FIG. 4 is a sectional view taken along line 4—4 of FIG. 2 of the interior of the inspection station showing the side cameras and back lights and the through beam sensor and displacement sensor.

FIG. 5 is a sectional view taken along line 5—5 of FIG. 2 showing the conveyor and inspection station with the top camera.

DETAILED DESCRIPTION OF THE PREFERRED EMBODIMENTS

The present invention is advantageous because it now allows high speed inspection of every container that is advanced along a conveyor into an inspection station. The invention is especially relevant to can manufacturing systems. Modern can manufacturing lines can produce cans at the rate of about 50 cans per second, and as many as 4.5 million cans in a 24-hour shift. In the past, statistical process control has only allowed a small number of cans to be drawn from the conveyor line and inspected.

Figure 3C:
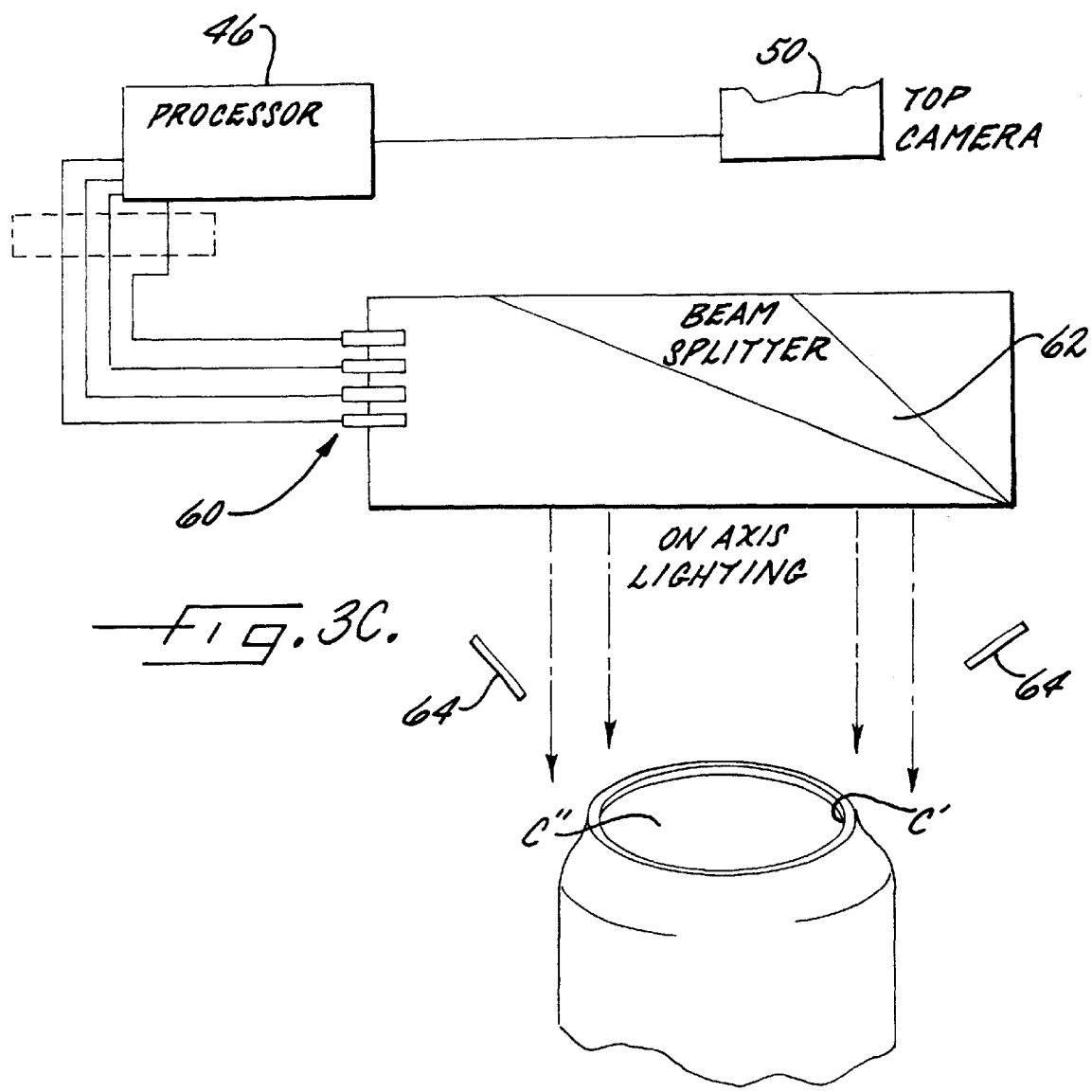
FIG. 3C is a schematic drawing of the beam splitter operation.
Figure 3D:
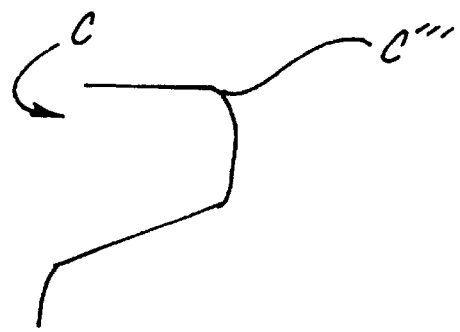
FIG. 3D is an enlarged schematic drawing of a flange used on a can.

Customers now require inspection of every can because of real world competition and budgetary constraints. For purposes of this description, cans such as used in the beverage industry, will be described. However, any type of container can be used with the system and method of the present invention. Typically, the cans and other similar containers include an inside surface C' and substantially cylindrical top opening C" and flange C'" formed at the top opening. An enlarged view shown in FIG. 3D of a flange C'" is illustrated. The flanges can naturally vary in configuration, but often are included because the soft human lips of an individual drinking from the beverage container extend over a flange. The flange provides safety and also manufacturing benefits, as known to those skilled in the art. The flange width can typically be about 0.080 inches. However, the critical dimensions are within ±0.0001 inch. Thus, any real time inspection process, as in the present invention, must account for those tolerance demands.

Figure 1:
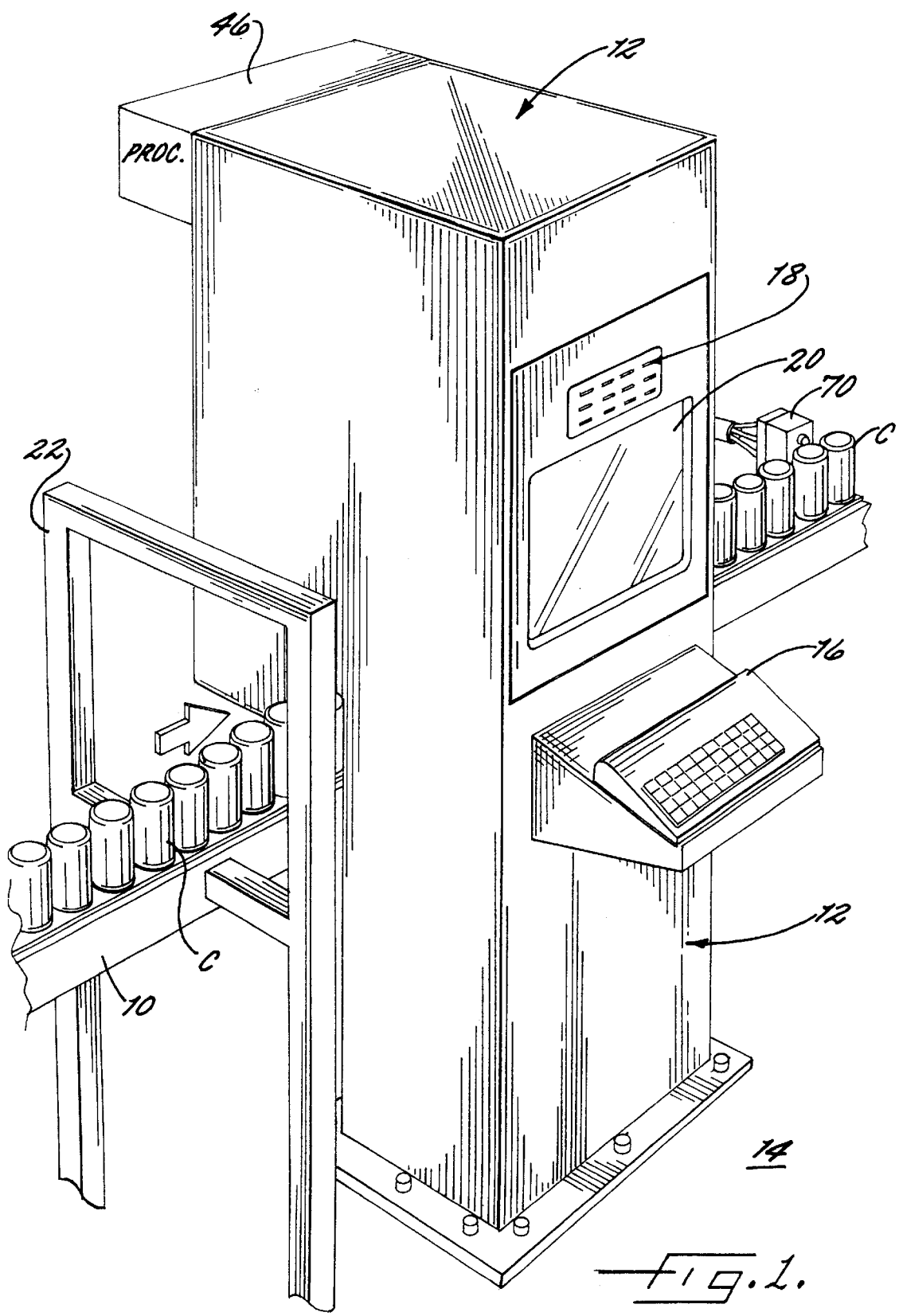
FIG. 1 is an isometric view of the inspection system of the present invention showing a conveyor that advances cans into the inspection station of the present invention.

Referring now to FIGS. 1 and 2, the overall large components used in the system and method of the present invention are illustrated. A conveyor 10 holds the cans C in vertical orientation and adjacent to each other and advances the plurality of cans along the predetermined path of travel defined by the conveyor into an inspection station indicated generally at 12. The inspection station 12 can be a separate unit that mounts over the conveyor 10 and is bolted to a floor 14. An operator console, such as a key pad 16 and/or touch screen 18, can be mounted at the inspection station 12. A see-through window 20 may provide for an operator "O" visual access into the interior of the inspection station 12. The conveyor 10 could be mounted on an appropriate frame 22 and suspension as known to those skilled in the art.

Figure 6:
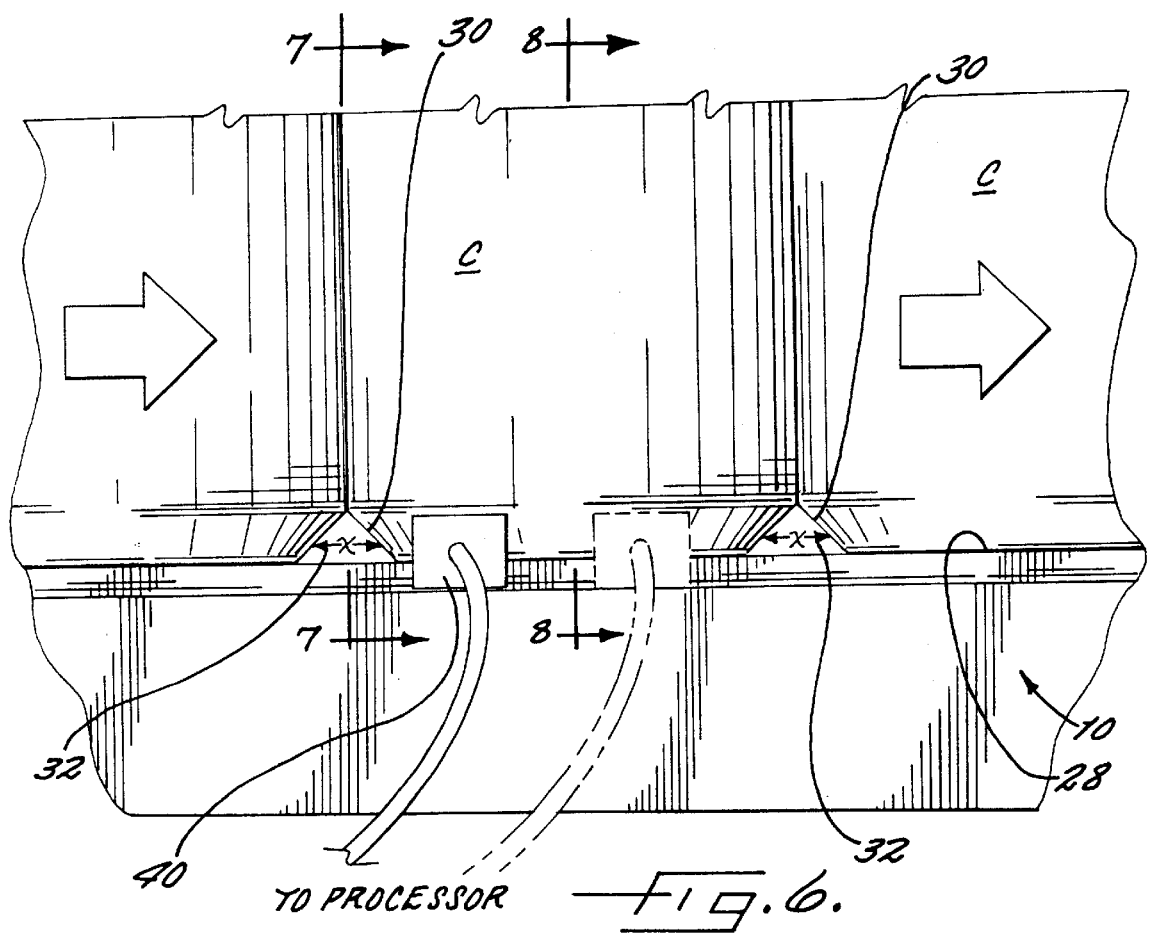
FIG. 6 is an enlarged view inside the inspection station showing the through beam sensor and displacement sensor.
Figures 7, 8:
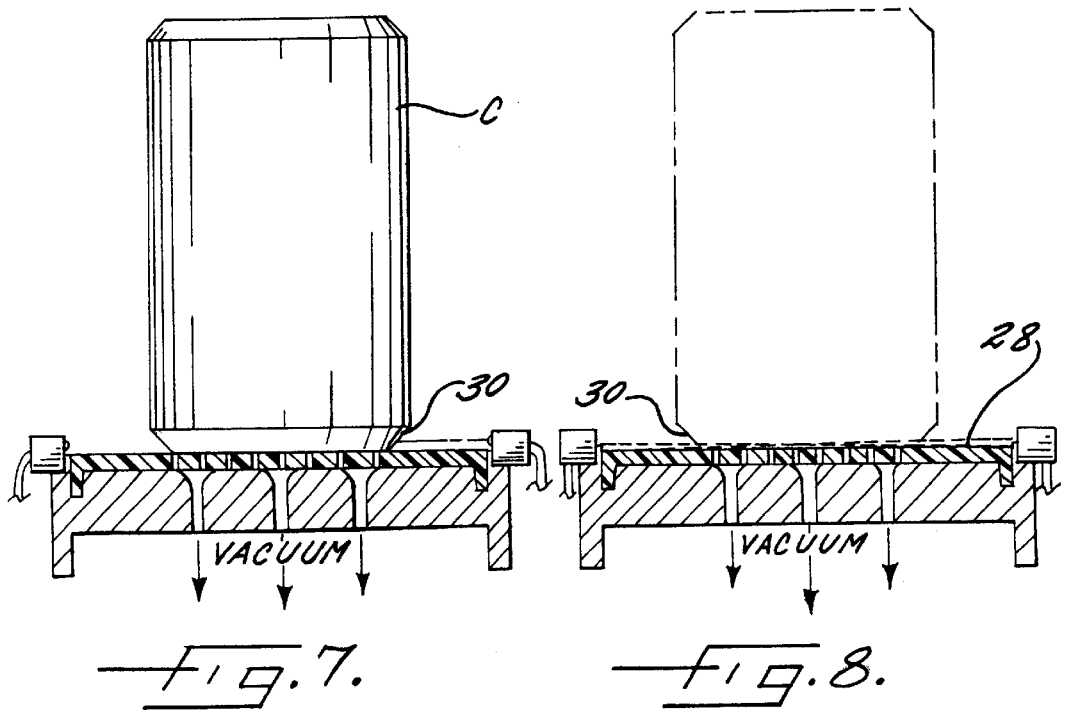
FIG. 7 is a sectional view taken along line 7—7 of FIG. 6 of a portion of the conveyor that can be used with the present invention and showing a vacuum draw onto the cans.
FIG. 8 is another sectional view taken along line 8—8 of FIG. 6 and showing the conveyor that can be used with the present invention.
Figure 9:
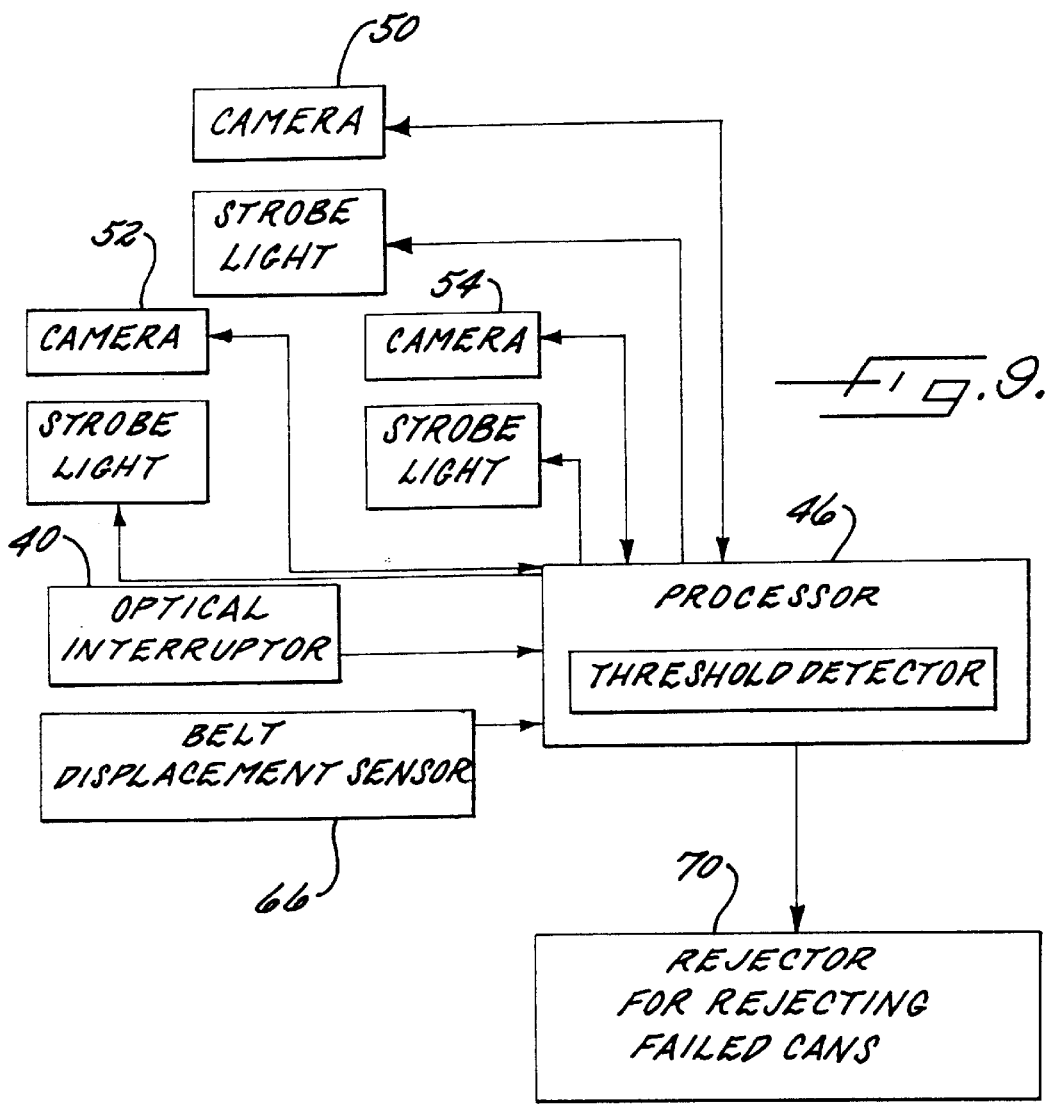
FIG. 9 is a block diagram showing the interconnection among the camera, strobe light, optical interrupter and other sensors and processors.

In one aspect of the present invention, the conveyor 10 includes a number of segments having vacuum holes 24 that connect to a vacuum system 26 to allow vacuum to be drawn down from the top surface 28 of the conveyor 10 to retain the can C against the top surface (FIGS. 7 and 8). The cans C also typically include a bottom bevel 30, such that when two cans are positioned in close proximity and touch each other, an open triangular area 32 defined by the dimension "X" in FIG. 6 is formed and can be adapted for use with a sensor, as will be explained below. The conveyor could be belt driven and move cans. Additionally, the vacuum could apply only minimal drawing force for can stability only, and cans could be advanced by pressure exerted from adjacent cans on a more stationary conveyor. It is also possible to use a conveyor that forces air upward against a can such that each can "floats" on the conveyor. Thus, if a straight line stationary conveyor is used or a curved stationary conveyor with side rails, the cans can "float" on the conveyor and be pushed along the air cushioned conveyor and into the inspection station 12. Other conveyors could be used as suggested by those skilled in the art.

Referring now to FIGS. 4 and 6, cans C are advanced into the inspection station 12. A through beam sensor 40 (e.g., belt displacement sensor) is positioned inside the inspection station 12 and includes a light source 42 positioned on one side of the conveyor and a light receptor 44 positioned on the other side of the conveyor. The through beam sensor 40 is positioned at the conveyor close to its top surface, such that when the "open" or triangular area 32 defined by the adjacent bottom bevels 30 of the two cans passes through the beam sensor, the light passes from the light source 42 through the area 32 defined by the letter X in FIG. 6 and is received by the light receptor 44 positioned on the other side of the conveyor. The through beam sensor 40 is connected to a processor 46 that performs the functions of the system and method of the present invention, as will be explained below. The inspection station 12 also includes a top camera 50 and two side cameras 52, 54. The top camera 50 is positioned to have a field of view looking down into the top opening of a can. The opposing side cameras 52, 54 are positioned on respective sides of the conveyor 10 and have a field of view in elevation of the can C. The top camera 50 is used to obtain pixel images of the top portion of the can as obtained from the top camera and obtain pixel images in elevation of the can from the two side cameras. Although different cameras can be used, it has been found that charge-coupled device (CCD) cameras are reliable and can be operated at the necessary speeds for the present invention as explained below.

At least one light source illuminates the exterior of the container and the interior of the container through the top opening after sensing that a container has advanced into the inspection area. In one illustrated aspect of the present invention, the light source includes a strobe light that could be formed as one strobe light or a plurality of strobe lights that flash at the same time at different angles against the can. In the embodiment of FIG. 4, a back light 56, which could be formed as a strobe light, is positioned adjacent each side camera 52, 54 and flashes when the through beam sensor 40 has sensed that a can C has entered the inspection station 12 and into the field of view of the cameras.

In still another aspect of the present invention, a top light source, indicated generally at 58, can provide on-axis lighting into the can, thus giving light that is on-axis with the cylindrical and vertical configuration of the can. In the schematic portion of the diagram shown in FIG. 3C, the on-axis lighting can include a plurality of fiber optic bundles 60, such as the illustrated four bundles, which generate light into a beam splitter 62 to allow a reflection on-axis into the can top opening. The beam splitter system could operate as white glass diffusion. It is also possible to use other light sources 64 that extend peripherally around the top opening of the can and illuminate down at an angle.

The strobe effect is produced by command signals generated from the processor, which connects to the respective light sources. At the same time, the cameras also acquire pixel images of the container. The pixel images are used to determine measurements of the can. For example, a certain number of pixels can correspond to a certain dimension in inches. As an example only, 12 pixels could correspond to 0.006 inches. Thus, the processor can have appropriate software, as can be developed by those skilled in the art, and be connected to the sensor and top and side cameras and process the pixel images and calculate the eccentricity, diameter of the opening, and flange width measurements based on the pixel image of the top and interior of the container. The processor also calculates height and flange angle measurements based on the pixel images obtained in elevation of the container. It is also possible to determine inside and outside dimensions of the container to determine what is known in the can manufacturing industry as the "plug diameter."

As noted before, CCD cameras can be used. As known to those skilled in the art, the charge-coupled device (CCD) camera uses the silicon light sensor to convert incident light or photons into electrons. Because of the high speed line operation, the two opposing side cameras can operate in a half resolution mode. Their camera field of vision is small and it is possible to use half the resolution and obtain the measurements desired with the pixel images. The top camera in one aspect of the invention, as an example, can be a "dual tap" camera. For example, instead of interlacing fields with updates every $\frac{1}{30}$ seconds, as in a normal television camera, a dual tap camera can have an output for each one of the frames and acquire them simultaneously instead of interlacing two frames. Thus, it is possible to send out the frames simultaneously on two different lines to allow imaging much faster. This is advantageous for the more complicated imaging of the top portion of the can. Because the pixel image is based on the entire top portion of the can, it is not desirable to use the top camera at half resolution. Preferably, a more exact full resolution camera mode is used.

The processor 46 can obtain the pixel images and processes those pixel images to calculate the eccentricity, diameter of the opening and flange width measurements based on the pixel image from the top and interior of the container. The processor also calculates height and flange angle measurements based on the pixel images obtained in the elevation of the container.

The software and system code can be developed by techniques known to those skilled in the art and written in C++. It is possible to use modified codes, such as from the image software produced and sold by Cognex Corporation of Natick, Mass. Such software that can be developed can relate to that type of software that is related to the "clamping tool" software disclosed in U.S. Pat. Nos. 5,818,443; 5,742,037; 5,901,241; 5,371,690; the disclosures which are hereby incorporated by reference in their entirety.

To ensure a proper height measurement, the position of the conveyor, such at its angle of inclination and its vertical position, is detected by a conveyor displacement sensor 66 (FIG. 6), also referred to as a belt displacement sensor when a belt is used for the conveyor. The conveyor displacement sensor 66 gives an indication of the position (and angle of a belt) at the top surface of the conveyor, thus, aiding in the imaging at high speed so that the proper height can be determined. This displacement measurement is then processed in the processor 46 with the pixel image to obtain a proper height measurement.

Figure 10:
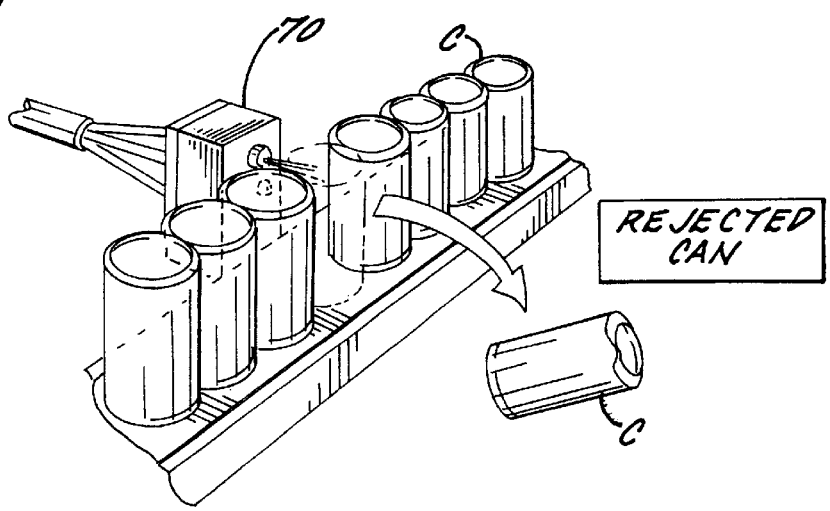
FIG. 10 is an isometric drawing showing the ejection station.

In operation, cans C are advanced into the inspection station 12 and sensed by the through beam sensor 40. The through beam sensor then triggers the light illumination, such as through the strobe light, and obtains pixel images from the three cameras. The processor processes the pixel images and includes a circuit for comparing the calculated measurements with the threshold measurement requirement. If the threshold measurement requirement is not met, then the processor counts the number of cans until the particular can that should be rejected enters an ejection station 70 where a pneumatic blow off tool 72 or other mechanism pushes the can off the conveyor (FIG. 10).

Figure 11:
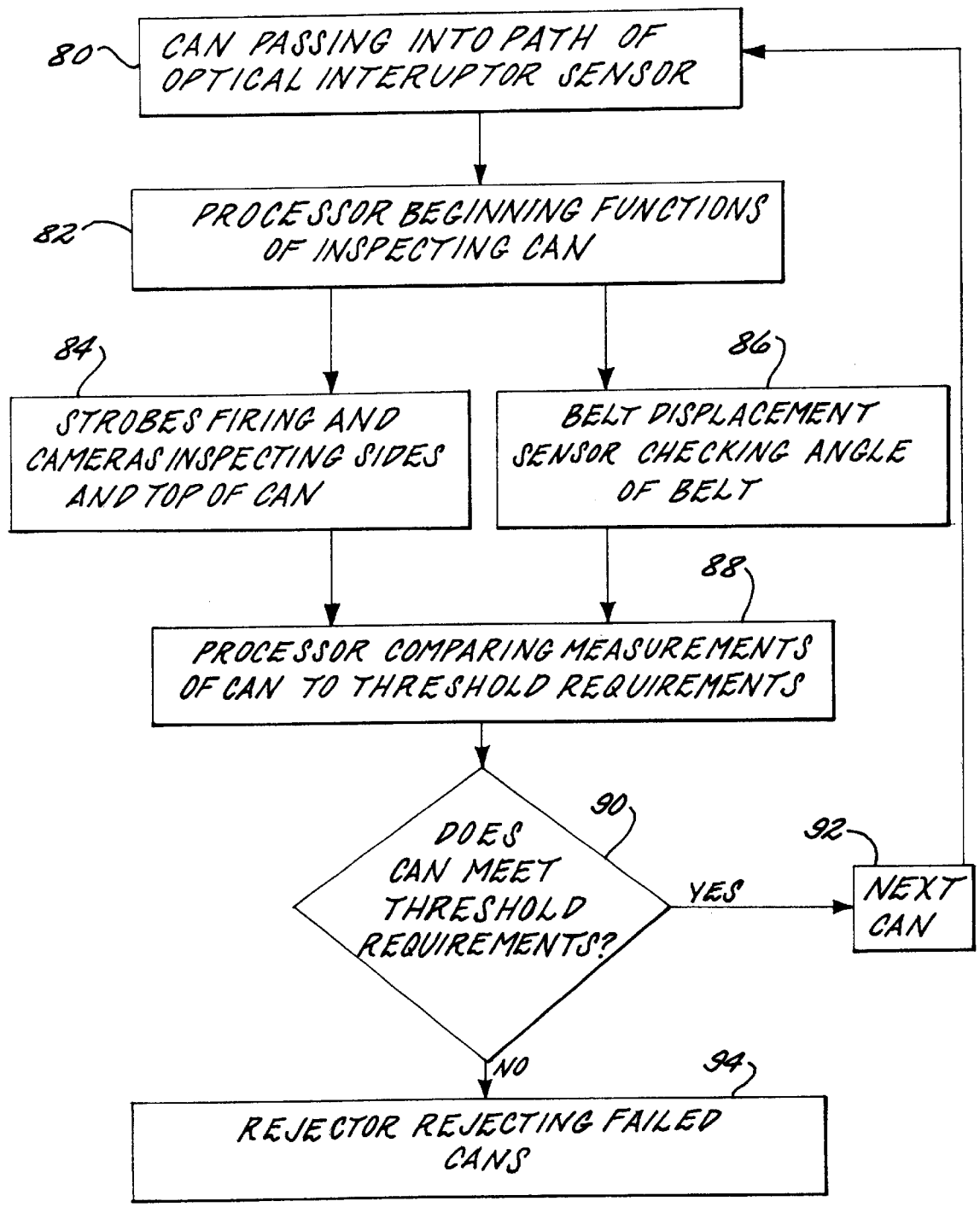
FIG. 11 is a high level flow chart illustrating the method of the present invention.

FIG. 11 illustrates a flow chart of the basic method that is used with the present invention. A can initially passes into the path of the optical interrupt sensor, also referred to as the through beam sensor (block 80). At this time, the processor begins its functions of inspecting the can (block 82) with the strobes firing and the cameras inspecting sides and top of can (block 84). At the same time, the conveyor or belt displacement sensor checks the angle of the belt (block 86). The processor compares the measurements of the can to the threshold requirements as shown in block 88. If the can does meet the threshold requirements as in block 90, then the next can is inspected (block 92). If the can does not meet the threshold requirements, then the rejector rejects the filled can, as shown in FIG. 10 at block 94.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A system for inspecting containers comprising:
    a conveyor for advancing a plurality of containers along a predetermined path of travel into an inspection area, wherein each container has a longitudinal axis and includes an inside surface and a substantially cylindrical top opening and a flange formed at the top opening;
    a sensor for sensing when a container has advanced into the inspection area;
    at least one upper light source for illuminating the interior of the container through the top opening after sensing that a container has advanced into the inspection area and including a beam splitter that receives the light from the at least one light source to allow reflection on-axis into the container top opening;
    a camera located at the inspection area and having a field of view looking down into the top opening for obtaining a pixel image of the top and interior of the container wherein each pixel corresponds to a predetermined dimension;
    opposing side cameras positioned on respective sides of the conveyor at the inspection area and having a field of view in elevation of the container for obtaining pixel images in elevation of the container and wherein each pixel corresponds to a predetermined dimension;
    opposing light sources positioned adjacent respective opposing side cameras that strobe in time with the sensing of a container to illuminate the exterior of the container, wherein the side cameras are timed to acquire pixel images at each strobing; and
    a processor connected to the sensor and top and side cameras for processing the pixel images and calculating the eccentricity, diameter of the opening and flange width measurements based on the pixel image of the top and interior of the container and calculating height and flange angle measurements based on the pixel images obtained in elevation of the container, said processor including a circuit for comparing the calculated measurements with a threshold measurement requirement.

2. A system according to claim 1, and further comprising a circuit for processing the pixel image obtained from the top camera for calculating the inside and outside diameter of the opening.

3. A system according to claim 1, wherein said light source further comprises a strobe light.

4. A system according to claim 1, and further comprising an ejection station for ejecting containers from off the conveyor when the calculated measurements are not within the threshold measurement requirement.

5. A system according to claim 1, wherein the cameras comprise charge-coupled device (CCD) cameras.

6. A system according to claim 1, wherein said sensor comprises a through beam sensor having a light source positioned on one side of said conveyor and a light receptor positioned on the other side of said conveyor.

7. A system for inspecting cans comprising:
    a conveyor for advancing a plurality of cans along a predetermined path of travel into an inspection area, wherein each can has a longitudinal axis and includes an inside surface and a substantially cylindrical top opening and a flange formed at the top opening;
    a sensor for sensing when a can has advanced into the inspection area;
    opposing light sources for illuminating the exterior of the can wherein the light sources strobe in time with the sensing of the container such that the can is illuminated as it travels into the inspection area;
    an upper light source for generating light with the can into the interior of the can through the top opening after sensing that a can has advanced into the inspection area and including a beam splitter that receives the light from the light source to allow reflection on-axis into the container top opening;
    a camera located at the inspection area and having a field of view looking down into the top opening for obtaining a pixel image of the top and interior of the can wherein each pixel corresponds to a predetermined dimension;
    opposing side cameras positioned on respective sides of the conveyor at the inspection area adjacent the opposing light sources and having a field of view in elevation of the can for obtaining pixel images in elevation of the can at the strobing of the light sources; and
    a processor connected to the sensor and top and side cameras for processing the pixel images and calculating the eccentricity, diameter of the opening and flange width measurements based on the pixel image of the top and interior of the container and calculating height and flange angle measurements based on the pixel images obtained in elevation of the container, said processor including a circuit for comparing the calculated measurements with a threshold measurement requirement.

8. A system according to claim 7, and further comprising a circuit for processing the pixel image obtained from the top camera for calculating the inside and outside diameter of the opening.

9. A system according to claim 7, wherein said light source further comprises a strobe light.

10. A system according to claim 7, and further comprising an ejection station for ejecting cans from off the conveyor when the calculated measurements are not within the threshold measurement requirement.

11. A system according to claim 7, wherein the cameras comprise charge-coupled device (CCD) cameras.

12. A system according to claim 7, and wherein said sensor comprises a through beam sensor having a light source positioned on one side of said conveyor and a light receptor positioned on the other side of said conveyor.

13. A method for inspecting containers comprising the steps of:
    feeding a plurality of containers along a predetermined path of travel into an inspection station, wherein the containers each have a longitudinal axis and include an inside surface having a substantially cylindrical top opening and a flange formed at the top opening;
    sensing a container as it advances into the inspection station;
    illuminating the interior of the container through the opening in response to the sensing of the container wherein each pixel corresponds to a predetermined dimension, while also obtaining a pixel image of the container from a top camera having a field of view looking down into the top opening by passing light through a beam splitter to allow reflection on-axis into the top opening of the container;

acquiring pixel images in side elevation by opposing cameras and adjacent, opposing strobe lights that illuminate the containers in side elevation as the cameras acquire pixel images, each pixel corresponding to a predetermined dimension;

processing the pixel images obtained from the top camera for calculating the eccentricity, the diameter of the opening and the flange width measurements and processing the pixel images obtained from the side cameras for calculating the height and flange angle measurements;

comparing the calculated measurements with a threshold measurement requirement; and rejecting the container when the container does not meet a threshold measurement.

14. A method according to claim 13, and further comprising the steps of processing the pixel images obtained from the top camera for calculating the inside and outside diameter of the opening.

15. A method according to claim 13, wherein the step of rejecting a container further comprises the step of ejecting the container from the predetermined path of travel at an ejection station located downstream from the predetermined path of travel.

16. A method according to claim 13, and further comprising the step of counting the number of cans from the inspection station to the ejection station to determine which rejected container is to be rejected.

17. A method according to claim 13, wherein the cameras further comprises charge-coupled device (CCD) cameras.

18. A method according to claim 13, and further comprising the step of sensing a container by a through beam sensor having a light source positioned on one side of the predetermined path of travel and a light receptor positioned on the other side of the predetermined path of travel.

19. A method according to claim 13, and further comprising the step of processing the pixel images obtained from the side cameras for determining sidewall anomalies.

20. A method for inspecting cans comprising the steps of:

feeding a plurality of cans along a conveyor into an inspection station, wherein the cans each have a longitudinal axis and include an inside surface having a substantially cylindrical top opening and a flange formed at the top opening;

sensing a can as it advances into the inspection station;

illuminating the interior of the can by generating light that is on-axis with the can and into the interior of the can by passing light through a beam splitter to allow reflection on-axis into the top opening of the can;

obtaining a pixel image of the can from a top camera having a field of view looking down into the top opening wherein each pixel corresponds to a predetermined dimension;

obtaining pixel images in side elevation of the can by opposing cameras and adjacent, opposing strobe lights that illuminate the container in side elevation as the cameras acquire pixel images, each pixel corresponding to a predetermined dimension;

processing the pixel images obtained from the top camera for calculating the eccentricity, the diameter of the opening and the flange width measurements and processing the pixel images obtained from the side cameras for calculating the height and flange angle measurements;

comparing the calculated measurements with a threshold measurement requirement; and rejecting the can when the can does not meet a threshold measurement.

21. A method according to claim 20, and further comprising the step of sensing the vertical position of the conveyor at the time of can sensing for use in determining the height of the can.

22. A method according to claim 20, wherein the step of illuminating the interior of the can on-axis with the can further comprises the step of passing light through a beam splitter positioned above the can.

23. A method according to claim 20, and further comprising the step of holding the cans onto the conveyor by vacuum.

24. A method according to claim 20, and further comprising the steps of processing the pixel images obtained from the top camera for calculating the inside and outside diameter of the opening.

25. A method according to claim 20, wherein the step of illuminating further comprises the step of illuminating the side of the can by a backlight positioned adjacent each side camera.

26. A method according to claim 20, wherein the step of illuminating further comprises the step of actuating a strobe light.

27. A method according to claim 20, wherein the step of rejecting a can further comprises the step of ejecting the can from the conveyor at an ejection station located downstream from the predetermined path of travel.

28. A method according to claim 20, and further comprising the step of counting the number of cans from the inspection station to the ejection station to determine which rejected can is to be rejected.

29. A method according to claim 20, wherein the cameras further comprises charge-coupled device (CCD) cameras.

30. A method according to claim 20, and further comprising the step of sensing the position of a lower end of the can during the step of forming pixel images.

31. A method according to claim 20, and further comprising the step of sensing a can by a through beam sensor having a light source positioned on one side of the predetermined path of travel and a light receptor positioned on the other side of other predetermined path of travel.

32. A method according to claim 31, and further comprising the step of feeding each can in adjacent contact to each other, each can including a bottom bevel, wherein the light beam extends through an open area formed by the bottom bevel of adjacent, contacting cans.

33. A method according to claim 20, and further comprising the step of processing the pixel images obtained from the side cameras for determining sidewall anomalies.

* * * * *